United States Patent
De Nanteuil et al.

(10) Patent No.: US 6,706,742 B2
(45) Date of Patent: Mar. 16, 2004

(54) ALPHA-AMINO-ACID COMPOUNDS

(75) Inventors: Guillaume De Nanteuil, Suresnes (FR); Bernard Portevin, Elancourt (FR); Alain Benoist, Franconville (FR); Nigel Levens, Vaucresson (FR); Olivier Nosjean, Rueil Malmaison (FR); Bernadette Husson-Robert, Nanterre (FR); Michelle Boulanger, Chatou (FR)

(73) Assignee: Les Laboratories Servier, Neuilly-sur-Seine (FR)

(*) Notice: Subject to any disclaimer, the term of this patent is extended or adjusted under 35 U.S.C. 154(b) by 18 days.

(21) Appl. No.: 10/146,272

(22) Filed: May 15, 2002

(65) Prior Publication Data

US 2003/0078247 A1 Apr. 24, 2003

(30) Foreign Application Priority Data

May 15, 2001 (FR) .............................. 01 06375

(51) Int. Cl.[7] .................... C07D 277/04; C07D 207/04; A61K 31/426
(52) U.S. Cl. .................. 514/365; 548/200; 548/540; 514/423
(58) Field of Search ................. 548/200, 540; 514/365, 423

(56) References Cited

U.S. PATENT DOCUMENTS 6,090,786 A * 7/2000 Augustyns et al. .......... 514/19

\* cited by examiner

*Primary Examiner*—Joseph K. McKane
*Assistant Examiner*—Golam M Shameem
(74) *Attorney, Agent, or Firm*—The Firm of Hueschen and Sage

(57) ABSTRACT

Compound selected from those of formula (I):

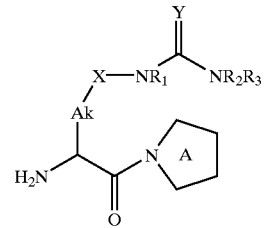

wherein:

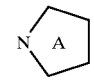

represents an optionally substituted 5-membered nitrogen-containing heterocycle, Ak represents an alkylene chain,
X represents a single bond or phenylene,
$R_1$ and $R_2$, which may be identical or different, each represent hydrogen or alkyl,
$R_3$ represents alkyl, nitro or cyano,
Y represents $NR_4$ or $CHNO_2$,
$R_4$ represents hydrogen or alkyl, its tautomers when they exist, its optical isomers, and addition salts thereof with a pharmaceutically acceptable acid, with the exclusion of compounds wherein, simultaneously,

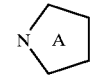

represents an unsubstituted 5-membered nitrogen-containing heterocycle, Ak represents $-(CH_2)_3-$, X represents a single bond, Y represents NH and $R_3$ represents nitro.

Medicinal products containing the same which are useful as dipeptidyl peptidase IV inhibitors.

13 Claims, No Drawings

ALPHA-AMINO-ACID COMPOUNDS

BACKGROUND OF THE INVENTION

Dipeptidyl peptidase IV is a membrane serine protease that is present in many human tissues and involved in numerous pathologies.

In particular, it has been shown that DPP IV is responsible for the inactivation of GLP-1 (glucagon-like peptide-1). GLP-1 is an important stimulator of the secretion of insulin in the pancreas and accordingly has a direct beneficial effect on the level of glucose in the blood.

Inhibition of DPP IV accordingly constitutes an extremely promising approach in the treatment of glucose intolerance and of disorders associated with hyperglycaemia, such as, for example, non-insulin-dependent diabetes (type II diabetes) or obesity.

DESCRIPTION OF THE PRIOR ART

DPP IV inhibitors have already been described in the literature, for example amide compounds in Patent Application EP 0 490 379 and in the journal Adv. Exp. Med. Biol. 1997, 421, 157–160, and carbamate compounds in Patent Application DE 19826972.

Moreover, α-amino acid compounds, analogues of arginine, have been described in Patent Application WO 96/27593 as inhibitors of NO-synthase, for use, as such, in the treatment of pathologies of the central and peripheral nervous systems, pathologies of dysfunctions of the gastrointestinal and urinary systems, and pathologies associated with the cardiovascular or bronchopulmonary system.

The compounds of the invention have dipeptidyl peptidase IV-inhibiting properties, which thus makes them especially useful in the treatment of glucose intolerance and disorders associated with hyperglycaemia.

DETAILED DESCRIPTION OF THE INVENTION

More especially, the present invention relates to compounds of formula (I):

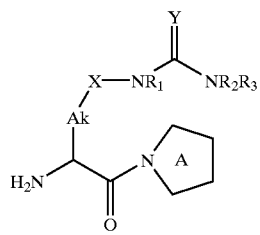

(I)

wherein:

represents a 5-membered nitrogen-containing heterocycle optionally substituted by a cyano group, Ak represents a linear or branched $(C_1-C_6)$alkylene chain, X represents a single bond or a phenylene group, $R_1$ and $R_2$, which may be identical or different, each represent a hydrogen atom or a linear or branched $(C_1-C_6)$alkyl group, Y represents $NR_4$ or $CH\text{—}NO_2$, $R_4$ represents a hydrogen atom or a linear or branched $(C_1-C_6)$alkyl group, $R_3$ represents:
a group selected from linear or branched $(C_1-C_6)$alkyl, nitro and cyano, when Y represents $CH\text{—}NO_2$, or
a group selected from nitro and cyano, when Y represents $NR_4$, their tautomers when they exist, their optical isomers, and addition salts thereof with a pharmaceutically acceptable acid, with the exclusion of compounds wherein, simultaneously,

represents an unsubstituted 5-membered nitrogen-containing heterocycle, Ak represents the group —$(CH_2)_3$—, X represents a single bond, Y represents NH and $R_3$ represents the nitro group.

Among the pharmaceutically acceptable acids, there may be mentioned by way of non-limiting example hydrochloric acid, hydrobromic acid, sulfuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid, oxalic acid, etc.

"5-membered nitrogen-containing heterocycle" is understood to mean a 5-membered saturated monocyclic group containing one, two or three hetero atoms, one of which hetero atoms is the nitrogen atom, and any additional hetero atoms present are selected from the atoms oxygen, nitrogen and sulphur.

The preferred 5-membered nitrogen-containing heterocycles are the groups pyrrolidinyl and thiazolidinyl.

The compounds of formula (I) wherein $R_2$ represents a hydrogen atom exist in two tautomeric forms represented by the formulae (Ia) and (Ib):

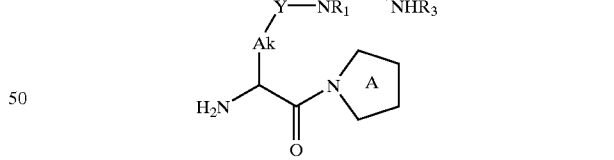

(Ia)

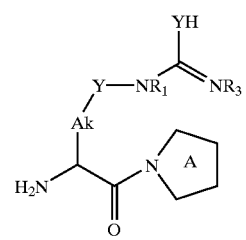

(Ib)

which both form an integral part of the invention.

The compounds of formula (I) wherein $R_3$ represents a hydrogen atom exist in two tautomeric forms represented by the formulae (Ic) and (Id):

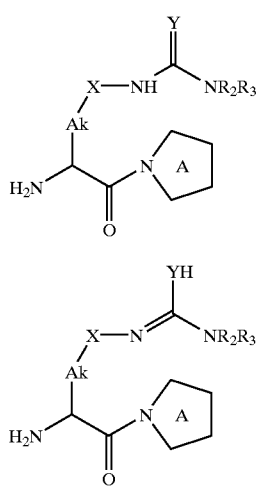
(Ic)

(Id)

which both form an integral part of the invention.

The preferred compounds of formula (I) are those wherein

represents a 1-pyrrolidinyl group optionally substituted by a cyano group, or a 1,3-thiazolidin-3-yl group optionally substituted by a cyano group.

The preferred compounds of formula (I) are those wherein the configuration α to the amide function is (S).

An advantageous aspect of the invention relates to compounds of formula (I) wherein Ak represents the group $(CH_2)_4$.

Another advantageous aspect of the invention relates to compounds of formula (I) wherein

represents a 1-pyrrolidinyl group substituted by a cyano group, or a 1,3-thiazolidin-3-yl group substituted by a cyano group, and Ak represents the group $(CH_2)_3$.

A further advantageous aspect of the invention relates to compounds of formula (I) wherein X represents a single bond.

A further advantageous aspect of the invention relates to compounds of formula (I) wherein Y represents a group $NR_4$, wherein $R_4$ represents a hydrogen atom or a linear or branched $(C_1-C_6)$alkyl group.

A further advantageous aspect of the invention relates to compounds of formula (I) wherein $R_3$ represents the nitro group.

Among the preferred compounds of the invention, there may be mentioned more especially:

N-{(4S)-4-amino-5-[(2S)-2-cyano-1-pyrrolidinyl]-5-oxopentyl}-N'-nitroguanidine, its tautomers, optical isomers, and addition salts thereof with a pharmaceutically acceptable acid, N-{(5S)-5-amino-6-[(2S)-2-cyano-1-pyrrolidinyl]-6-oxohexyl}-N'-nitroguanidine, its tautomers, optical isomers, and addition salts thereof with a pharmaceutically acceptable acid, and N-{(5S)-5-amino-6-(1,3-thiazolidin-3-yl)-6-oxohexyl}-N'-nitroguanidine, its tautomers, optical isomers, and addition salts thereof with a pharmaceutically acceptable acid.

The invention relates also to a process for the preparation of compounds of formula (I), characterised in that a compound of formula (II):

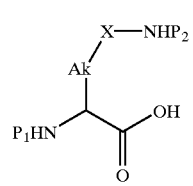
(II)

wherein Ak and X are as defined for formula (I), $P_1$ represents an amino-function-protecting group, and $P_2$ represents an amino-function-protecting group other than $P_1$, is reacted with a compound of formula (III):

(III)

wherein

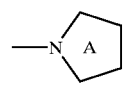

is as defined for formula (I), under conventional peptide coupling conditions, to yield, after deprotection, a compound of formula (IV),

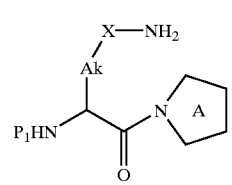
(IV)

wherein

, $P_1$, Ak and X are as defined hereinbefore, which is then converted, by conventional organic chemistry reactions, followed by a deprotection reaction, to a compound of formula (I), which is purified, if necessary, according to a conventional purification technique, separated, if desired, into its optical isomers according to a conventional separation technique, and converted, if desired, into addition salts thereof with a pharmaceutically acceptable acid.

The compounds of formula (Ie), a particular case of the compounds of formula (I):

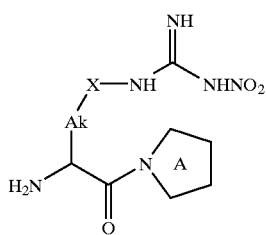

wherein

$R_1$, Ak and X are as defined for formula (I), can also be obtained starting from the compound of formula (V):

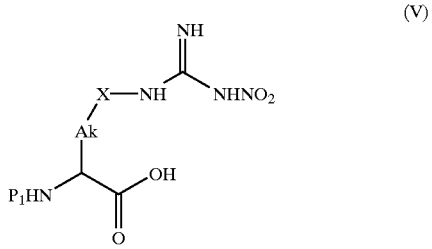

wherein $P_1$, Ak and X are as defined hereinbefore, which is reacted with a compound of formula (III), under conventional peptide coupling conditions, to yield, after deprotection where necessary, a compound of formula (Ie), which is purified, if necessary, according to a conventional purification technique, separated, if desired, into its optical isomers according to a conventional separation technique, and converted, if desired, into addition salts thereof with a pharmaceutically acceptable acid.

The compounds of the present invention, in addition to being new, have pharmacologically valuable properties. They have dipeptidyl peptidase IV-inhibiting properties which make them useful in the treatment of glucose intolerance and of disorders associated with hyperglycaemia, such as type II diabetes or obesity.

The invention relates also to pharmaceutical compositions comprising as active ingredient at least one compound of formula (I) with one or more suitable inert, non-toxic excipients. Among the pharmaceutical compositions according to the invention, there may be mentioned more especially those that are suitable for oral, parenteral (intravenous, intramuscular or subcutaneous) or nasal administration, tablets or dragées, sublingual tablets, gelatin capsules, lozenges, suppositories, injectable preparations, drinkable suspensions, etc.

The useful dosage can be adapted according to the nature and severity of the disorder, the route of administration and the age and weight of the patient and any associated treatments. The dosage varies from 0.5 mg to 2 g per 24 hours in one or more administrations.

The following Examples illustrate the invention and do not limit it in any way.

The starting materials used are known products or are prepared according to known procedures.

The structures of the compounds described in the Examples were determined according to the usual spectrometric techniques (infrared, NMR, mass spectrometry).

The expression "compound of configuration (2α) or (2β)" is understood to mean a compound selected from the compounds of absolute configurations (2R) and (2S), it being understood that when compound (2α) represents the compound of absolute configuration (2R), then compound (2β) represents the compound (2S).

EXAMPLE 1

N-{(4S)-4-Amino5-[(2S)-2-cyano-1-pyrrolidinyl]-5-oxopentyl}-N'-nitroguanidine Hydrochloride Step A: N-{(4S)-4-[(Tert-butyloxycarbonyl)-amino]-5-[(2S)-2-cyano-1-pyrrolidinyl]-5-oxopentyl}-N'-nitroguanidine 10 mmol of(2S)-2-cyano-pyrrolidine, 10 mmol of 1-hydroxybenzotriazole and 10 mmol of dicyclohexylcarbodiimide are added to 10 mmol of $N^2$-(tert-butyloxycarbonyl)-$N^5$-[(imino)-(nitroamino)-methyl]-ornithine dissolved in dimethylformamide. After stirring overnight at room temperature, the dicyclohexylurea that has formed is filtered off and then the dimethylformamide is removed by evaporation. The resulting residue is purified by chromatography over silica (eluant: dichloromethane/ethanol 95/5) to yield the expected product.

Step B: N-{(4S)-4-Amino-5-[(2S)-2-cyano-1-pyrrolidinyl]-5-oxopentyl}-N'-nitroguanidin hydrochloride A 4N solution of hydrochloric acid in dioxane is added to 10 mmol of the compound obtained in the preceding Step dissolved in dioxane. After stirring for 24 hours at room temperature, the solvent is removed by evaporation, water is added and the solution is lyophilised to yield the expected product.

| | Elemental microanalysis: | | | |
|---|---|---|---|---|
| | C % | H % | N % | Cl % |
| calculated | 39.58 | 6.04 | 29.37 | 10.62 |
| found | 40.35 | 6.00 | 29.00 | 10.90 |

EXAMPLE 2

N-[(4S)-4-Amino-5-(1-pyrrolidinyl)-5-oxopentyl]-N'-cyanoguanidine sesquihydrochloride Step A: 1-[(S)-$N^5$-(Benzyloxycarbonyl)-$N^2$-(tert-butyloxycarbonyl)-ornithyl]-pyrrolidine The expected product is obtained according to the process described in Step A of Example 1 starting from (S)-$N^5$-(benzyloxycarbonyl)-$N^2$-(tert-butyloxycarbonyl)-ornithine and pyrrolidine.

Step B: 1-[(S)-$N^2$-(Tert-butyloxycarbonyl)-ornithyl]-pyrrolidine 10 mmol of the compound obtained in the preceding Step dissolved in ethanol are hydrogenated in the presence of 10% palladium-on-carbon, at room temperature and ambient pressure, for 6 hours. The reaction mixture is then filtered and evaporated and then, after the addition of water, lyophilised to yield the expected product.

Step C: N-{(4S)-4-[(Tert-butyloxycarbonyl)-amino]-5-(1-pyrrolidinyl)-5-oxopentyl}-N'-cyanoguanidine The expected product is obtained according to the process described in Synthesis 1975, 332, starting from the compound obtained in the preceding Step and NaN(CN)$_2$.

Step D: N-[(4S)-4-Amino-5-(1-pyrrolidinyl)-5-oxopentyl]-N'-cyanoguanidine sesquihydrochloride The expected product is obtained according to the process described in Step B of Example 1 starting from the compound obtained in the preceding Step.

Elemental microanalysis:

|  | C % | H % | N % | Cl % |
|---|---|---|---|---|
| calculated | 43.03 | 7.06 | 27.37 | 17.32 |
| found | 43.26 | 7.23 | 26.82 | 16.85 |

EXAMPLE 3

N-[(4S)-4-Amino-5-(1,3-thiazolidin-3-yl)-5oxopentyl]-N'-cyanoguanidine

Step A: 3-{(S)-$N^5$-(Tert-butyloxycarbonyl)-$N^2$-[(9H-fluoren-9-yl-methoxy)-carbonyl]-ornithyl}-1,3-thiazolidine The expected product is obtained in accordance with the process described in Step A of Example 1 starting from (S)-$N^5$-(tert-butyloxycarbonyl)-$N^2$-(9H-fluoren-9-yl-methoxy)-carbonyl]-ornithine and 1,3-thiazolidine.

Step B: 3-{(S)-$N^2$-[(9H-Fluoren-9-yl-methoxy)-carbonyl]-ornithyl}-1,3-thiazolidine hydrochloride The expected product is obtained according to the process described in Step B of Example 1 starting from the compound obtained in the preceding Step.

Step C: N-[(4S)-4-Amino-5-(1,3-thiazolidin-3-yl)-5-oxopentyl]-N'-cyanoguanidine

The expected product is obtained according to the process described in Synthesis 1975, 332, starting from the compound obtained in the preceding Step and $NaN(CN)_2$.

Elemental microanalysis:

|  | C % | H % | N % | S % |
|---|---|---|---|---|
| calculated | 44.43 | 6.71 | 31.08 | 11.86 |
| found | 44.41 | 6.68 | 30.18 | 10.52 |

EXAMPLE 4

N-[(5S)-5-Amino-6-(1-pyrrolidinyl)-6-oxohexyl]-N'-cyanoguanidine hydrochloride

The expected product is obtained according to the process described in Example 2, replacing (S)-$N^5$-(benzyloxycarbonyl)-$N^2$-(tert-butyloxycarbonyl)-ornithine by (S)-$N^6$-(benzyloxy-carbonyl)-$N^2$-(tert-butyloxycarbonyl)-lysine.

EXAMPLE 5

$N^1$-[(4S)-4-Amino-5-(1-pyrrolidinyl)-5-oxopentyl]-$N_2$-methyl-2-nitro-1,1-ethylenediamine dihydrochloride Step A: 1-[(S)-$N^5$-(Benzyloxycarbonyl)-$N^2$-(tert-butyloxycarbonyl)-ornithyl]-pyrrolidine The expected product is obtained according to the process described in Step A of Example 1 starting from (S)-$N^5$-(benzyloxycarbonyl)-$N^2$-(tert-butyloxycarbonyl)-ornithine and pyrrolidine.

Step B: 1-[(S)-$N^2$-(Tert-butyloxycarbonyl)-ornithyl]-pyrrolidine 10 mmol of the compound obtained in the preceding Step dissolved in ethanol are hydrogenated in the presence of 10% palladium-on-carbon, at room temperature and ambient pressure, for 6 hours. The reaction mixture is then filtered and evaporated and then, after the addition of water, lyophilised to yield the expected product.

Step C: $N^1$-{(4S)-4-[(Tert-butyloxycarbonyl)-amino]-5-(1-pyrrolidinyl)-5-oxopentyl}-$N^2$-methyl-2-nitro-1,1-ethylenediamine The expected product is obtained according to the process described in Bioorg. Med. Chem. 1997, 7 (23), 3045–3048, starting from the compound obtained in the preceding Step and N-methyl-1-methylthio-2-nitro-ethyleneamine.

Step D: N1-[(4S)-4-Amino-5-(1-pyrrolidinyl)-5-oxopentyl]-N2-methyl-2-nitro-1,1-ethylenediamine dihydrochloride The expected product is obtained according to the process described in Step B of Example 1 starting from the compound obtained in the preceding Step.

Elemental microanalysis:

|  | C % | H % | N % |
|---|---|---|---|
| calculated | 40.23 | 7.03 | 19.55 |
| found | 40.17 | 6.98 | 18.92 |

EXAMPLE 6

N-[(4S)-4-Amino-5-(1-pyrrolidinyl)-5-oxopentyl]-N"-cyano-N'-methylguanidine hydrochloride Step A: 1-[(S)-$N^5$-(Benzyloxycarbonyl)-$N^2$-(tert-butyloxycarbonyl)-ornithyl]-pyrrolidine The expected product is obtained according to the process described in Step A of Example 1, starting from (S)-$N^5$-(benzyloxycarbonyl)-$N^2$-(tert-butyloxycarbonyl)-omithine and pyrrolidine.

Step B: 1-[(S)-$N^2$-(Tert-butyloxycarbonyl)-ornithyl]-pyrrolidine 10 mmol of the compound obtained in the preceding Step dissolved in ethanol are hydrogenated in the presence of 10% palladium-on-carbon, at room temperature and ambient pressure, for 6 hours. The reaction mixture is then filtered and evaporated and then, after the addition of water, lyophilised to yield the expected product.

Step C: N-{(4S)-4-[(Tert-butyloxycarbonyl)-amino]-5-(1-pyrrolidinyl)-5-oxopentyl}-N"-cyano-N'-methylguanidine The expected product is obtained according to the process described in Chem. Pharm. Bull. 1997, 45 (1), 53–61, starting from the compound obtained in the preceding Step, N-cyanoimido-S,S-dimethyldithiocarbonate and methylamine.

Step D: N-[(4S)-4-Amino-5-(1-pyrrolidinyl)-5-oxopentyl]-N"-cyano-N'''-methyl-guanidine hydrochloride The expected product is obtained according to the process described in Step B of Example 1, starting from the compound obtained in the preceding Step.

Mass spectrometry: [M+H]+=267; [M+Cl]+=301; [M−H]−=265.

EXAMPLE 7

N-{(4S)-4-Amino-5-[(4R)-4-cyano-1,3-thiazolidin-3-yl]-5-oxopentyl}-N'-nitroguanidine hydrochloride The expected product is obtained according to the process described in Example 1, replacing (2S)-2-cyano-pyrrolidine by (4R)-4-cyano-1,3-thiazolidine.

Elemental microanalysis:

|  | C % | H % | N % | S % | Cl % |
|---|---|---|---|---|---|
| calculated | 34.14 | 5.16 | 27.87 | 9.11 | 10.08 |
| found | 34.32 | 5.11 | 27.70 | 9.23 | 10.44 |

EXAMPLE 8

N-{(4S)-4-Amino-5-[(2α)-2-cyano-1,3-thiazolidin-3-yl]-5-oxopentyl}-N'-nitroguanidine hydrochloride Step A: N-{(4S)-4-[(Tert-butyloxycarbonyl)-amino]-5-[2-carbamoyl-1,3-thiazolidin-3-yl]-5-oxopentyl}-N'-nitroguanidine hydrochloride The expected product is obtained according to the process described in Step A of Example 1, replacing (2S)-2-cyano-pyrrolidine by (±)-1,3-thiazolidine-2-carboxamide.

Step B: N-{(4S)-4-[(Tert-butyloxycarbonyl)-amino]-5-[(2α)-2-carbamoyl-1,3-thiazolidin-3-yl]-5-oxopentyl}-N'-nitroguanidine hydrochloride The mixture of diastereoisomers obtained in the preceding Step A is separated by chromatography over silica (eluant:dichloromethane/methanol/NH$_4$OH 90/10/0.5). The expected product is the first of the diastereoisomers separated in that manner.

Step C: N-{(4S)-4-[(Tert-butyloxycarbonyl)-amino]-5-[(2α)-2-cyano-1,3-thiazolidin-3-yl]-5-oxopentyl}-N'-nitroguanidine 20 mmol of imidazole are added to 10 mmol of the compound obtained in the preceding Step dissolved in pyridine, and then the reaction mixture is cooled to −30° C., and 40 mmol of POCl$_3$ are added dropwise. The temperature is then brought to −20° C. in the course of 1 hour. The pyridine is then removed by evaporation, and the residue is dissolved in ethyl acetate. The solution is washed, dried and evaporated, and the resulting residue is purified by chromatography over silica (eluant:dichloromethane/methanol/NH$_4$OH 95/5/0.5) to yield the expected product.

Step D: N-{(4S)-4-Amino-5-[(2α)-2-cyano-1,3-thiazolidin-3-yl]-5-oxopentyl}-N'-nitroguanidine hydrochloride The expected product is obtained according to the process described in Step B of Example 1, starting from the compound obtained in the preceding Step C.

Elemental microanalysis:

|  | C % | H % | N % | S % | Cl % |
|---|---|---|---|---|---|
| calculated | 34.14 | 5.16 | 27.87 | 9.11 | 10.08 |
| found | 34.41 | 4.93 | 27.67 | 9.35 | 9.71 |

EXAMPLE 9

N-{(4S)-4-Amino-5-[(2β)-2-cyano-1,3-thiazolidin-3-yl]-5-oxopentyl}-N'-nitroguanidine hydrochloride The expected product is obtained according to the process described in Steps C and D of Example 8, starting from the second of the diastereoisomers separated in Step B of Example 8.

Mass spectrometry: LC/ESI/HR and MS/MS: [M+H]+=316.

EXAMPLE 10

N-[(5S)-5-Amino-6-(1-pyrrolidinyl)-6-oxohexyl]-N'-nitroguanidine hydrochloride

The expected product is obtained according to the process described in Example 1, starting from N$^2$-(tert-butyloxycarbonyl)-N$^6$-[(imino)-(nitroamino)-methyl]-lysine and pyrrolidine.

EXAMPLE 11

N-{(5S)-5-Amino-6-[(2S)-2-cyano-1-pyrrolidinyl]-6-oxohexyl}-N'-nitroguanidine hydrochloride The expected product is obtained according to the process described in Example 1, starting from N$^2$-(tert-butyloxycarbonyl)-N$^6$-[(imino)-(nitroamino)-methyl]-lysine and (2S)-2-cyano-pyrrolidine.

Elemental microanalysis:

|  | C % | H % | N % | Cl % |
|---|---|---|---|---|
| calculated | 41.44 | 6.38 | 28.19 | 10.19 |
| found | 41.66 | 6.31 | 27.78 | 10.18 |

EXAMPLE 12

N-[(5S)-5-Amino-6-(1,3-thiazolidin-3-yl)-6-oxohexyl]-N'-nitroguanidine hydrochloride The expected product is obtained according to the process described in Example 1 starting from N$^2$-(tert-butyloxycarbonyl)-N$^6$-[(imino)-(nitroamino)-methyl]-lysine and 1,3-thiazolidine.

Mass spectrometry: [M+H]+=305, [M−H]−=303

EXAMPLE 13

N-{(5S)-5-Amino-6-[(4R)-4-cyano-1,3-thiazolidin-3-yl]-6-oxohexyl}-N'-nitroguanidine hydrochloride The expected product is obtained according to the process described in Example 1, starting from N$^2$-(tert-butyloxycarbonyl)-N$^6$-[(imino)-(nitroamino)-methyl]-lysine and (4R)-4-cyano-1,3-thiazolidine.

Elemental microanalysis:

|  | C % | H % | N % | S % | Cl % |
|---|---|---|---|---|---|
| calculated | 36.11 | 5.51 | 26.80 | 8.76 | 9.69 |
| found | 36.36 | 5.49 | 26.68 | 8.81 | 10.04 |

EXAMPLE 14

N-{(5S)-5-Amino-6-[(2α)-2-cyano-1,3-thiazolidin-3-yl]-6-oxohexyl}-N'-nitroguanidine hydrochloride Step A: N-{(5S)-5-[(Tert-butyloxycarbonyl)-amino]-6-[2-carbamoyl-1,3-thiazolidin-3-yl]-6-oxohexyl}-N'-nitroguanidine hydrochloride The expected product is obtained according to the process described in Step A of Example 1, starting from N$^2$-(tert-butyloxycarbonyl)-N⁶-[(imino)-(nitroamino)-methyl]-lysine and (±)-1,3-thiazolidine-2-carboxamide.

Step B: N-{(5S)-5-[(Tert-butyloxycarbonyl)-amino]-6-[(2α)-2-carbamoyl-1,3-thiazolidin-3-yl]-6-oxohexyl}-N'-nitroguanidine hydrochloride The mixture of diastereoisomers obtained in the preceding Step A is separated by chromatography over silica (eluant: dichloromethane/methanol/NH₄OH 90/10/0.5). The expected product is the first of the diastereoisomers separated in that manner.

Step C: N-{(5S)-5-Amino-6-[(2α)-2-cyano-1,3-thiazolidin-3-yl]-6-oxohexyl}-N'-nitroguanidine hydrochloride The expected product is obtained according to the process described in Steps C and D of Example 8 starting from the compound obtained in the preceding Step.

Elemental microanalysis:

| | C % | H % | N % | S % | Cl % |
|---|---|---|---|---|---|
| calculated | 36.11 | 5.51 | 26.80 | 8.76 | 9.69 |
| found | 36.52 | 5.49 | 26.85 | 9.26 | 9.51 |

EXAMPLE 15

N-{(5S)-5-Amino-6-[(2β)-2-cyano-1,3-thiazolidin-3-yl]-6-oxohexyl}-N'-nitroguanidine hydrochloride The expected product is obtained according to the process described in Steps C and D of Example 8, starting from the second of the diastereoisomers separated in Step B of Example 14.

Elemental microanalysis:

| | C % | H % | N % | S % | Cl % |
|---|---|---|---|---|---|
| calculated | 36.11 | 5.51 | 26.80 | 8.76 | 9.69 |
| found | 36.50 | 5.49 | 26.00 | 9.66 | 9.66 |

EXAMPLE 16

N-{(4S)-4-Amino-5-[(2S)-2-cyano-1-pyrrolidinyl]-5-oxopentyl}-N'-cyanoguanidine sesquihydrochloride The expected product is obtained according to the process described in Example 2 starting from (S)-N⁵-(benzyloxycarbonyl)-N²-(tert-butyloxycarbonyl)-ornithine and (2S)-2-cyano-pyrrolidine.

Elemental microanalysis:

| | C % | H % | N % | Cl % |
|---|---|---|---|---|
| calculated | 43.03 | 7.06 | 27.37 | 17.32 |
| found | 43.26 | 7.23 | 26.82 | 16.85 |

EXAMPLE 17

N-{(5S)-5-Amino-6-[(2S)-2-cyano-1-pyrrolidinyl]-6-oxohexyl}-N'-cyanoguanidine hydrochloride The expected product is obtained according to the process described in Example 2 starting from (S)-N⁶-(benzyloxycarbonyl)-N²-(tert-butyloxycarbonyl)-lysine and (2S)-2-cyano-pyrrolidine.

Mass spectrometry: [M+H]+=292, [M−H]−=290

EXAMPLE 18

N-[(5S)-5-Amino-6-(1,3-thiazolidin-3-yl)-6-oxohexyl]-N'-cyanoguanidine hydrochloride The expected product is obtained according to the process described in Example 2 starting from (S)-N⁶-(benzyloxycarbonyl)-N²-(tert-butyloxycarbonyl)-lysine and 1,3-thiazolidine.

EXAMPLE 19

N¹-[(4S)-4-Amino-5-(1,3-thiazolidin-3-yl)-5-oxopentyl]-N²-methyl-2-nitro-1,1-ethylenediamine dihydrochloride The expected product is obtained according to the process described in Example 5, starting from (S)-N⁵-(benzyloxycarbonyl)-N²-(tert-butyloxycarbonyl)-ornithine and 1,3-thiazolidine.

Elemental microanalysis:

| | C % | H % | N % | S % | Cl % |
|---|---|---|---|---|---|
| calculated | 35.11 | 6.16 | 18.61 | 8.52 | 18.84 |
| found | 35.54 | 5.99 | 18.04 | 8.61 | 19.51 |

EXAMPLE 20

N¹-[(5S)-5-Amino-6-(1-pyrrolidinyl)-6-oxohexyl]-N²-methyl-2-nitro-1,1-ethylenediamine dihydrochloride The expected product is obtained according to the process described in Example 5, starting from (S)-N⁶-(benzyloxycarbonyl)-N²-(tert-butyloxycarbonyl)-lysine and pyrrolidine.

Elemental microanalysis:

| | C % | H % | N % | Cl % |
|---|---|---|---|---|
| calculated | 41.94 | 7.31 | 18.81 | 19.05 |
| found | 41.87 | 7.26 | 18.34 | 19.75 |

EXAMPLE 21

N¹-{(5S)-5-Amino-6-[(2S)-2-cyano-pyrrolidinyl]-6-oxohexyl}-N²-methyl-2-nitro-1,1-ethylenediamine dihydrochloride The expeted product is obtained according to the process described in Example 5, starting from (S)-N⁶-(benzyloxycarbonyl)-N²-(tert-butyloxycarbonyl)-lysine and (2S)-2-cyano-pyrrolidine.

Mass spectrometry: ESI/FIA/HR and MS/MS: [M+H]+=325; [M+Na]+=347.

EXAMPLE 22

N¹-[(5S)-5-Amino-6-(1,3-thiazolidin-3-yl)-6-oxohexyl]-N²-methyl-2-nitro-1,1-ethylenediamine dihydrochloride The expected product is obtained according to the process described in Example 5, starting from (S)-N⁶-

(benzyloxycarbonyl)-$N^2$-(tert-butyloxycarbonyl)-lysine and 1,3-thiazolidine.

Elemental microanalysis:

|  | C % | H % | N % | S % | Cl % |
|---|---|---|---|---|---|
| calculated | 36.93 | 6.46 | 17.94 | 8.22 | 18.17 |
| found | 37.08 | 6.49 | 17.17 | 8.11 | 18.63 |

EXAMPLE 23

N-{(4S)-4-Amino-5-[(2S)-2-cyano-1-pyrrolidinyl]-5-oxopentyl}-N''-cyano-N'-methylguanidine dihydrochloride The expected product is obtained according to the process described in Example 6, starting from (S)-$N^5$-(benzyloxycarbonyl)-$N^2$-(tert-butyloxycarbonyl)-ornithine and (2S)-2-cyano-pyrrolidine.

EXAMPLE 24

N-[(4S)-4-Amino-5-(1,3-thiazolidin-3-yl)-5-oxopentyl]-N''-cyano-N'-methylguanidine hydrochloride The expected product is obtained according to the process described in Example 6, starting from (S)-$N^5$-(benzyloxycarbonyl)-$N^2$-(tert-butyloxycarbonyl)-ornithine and 1,3-thiazolidine.

EXAMPLE 25

N-[(5S)-5-Amino-6-(1-pyrrolidinyl)-6-oxohexyl]-N''-cyano-N'-methylguanidine hydrochloride The expected product is obtained according to the process described in Example 6, starting from (S)-$N^6$-(benzyloxycarbonyl)-$N^2$-(tert-butyloxycarbonyl)-lysine and pyrrolidine.

EXAMPLE 26

N-{(5S)-5-Amino-6-[(2S)-2-cyano-1-pyrrolidinyl]-6-oxohexyl}-N''-cyano-N'-methylguanidine hydrochloride The expected product is obtained according to the process described in Example 6, starting from (S)-$N^6$-(benzyloxycarbonyl)-$N^2$-(tert-butyloxycarbonyl)-lysine and (2S)-2-cyano-pyrrolidine.

EXAMPLE 27

N-[(5S)-5-Amino-6-(1,3-thiazolidin-3-yl)-6-oxohexyl]-N''-cyano-N'-methylguanidine hydrochloride The expected product is obtained according to the process described in Example 6, starting from (S)-$N^6$-(benzyloxycarbonyl)-$N^2$-(tert-butyloxycarbonyl)-lysine and 1,3-thiazolidine.

EXAMPLE 28

N-{4-[(2S)-2-Amino-3-((2S)-2-cyano-1-pyrrolidinyl)-3-oxopropyl]-phenyl}-N''-cyano-N'-methylguanidine hydrochloride The expected product is obtained according to the process described in Example 6, starting from (S)-4-[(benzyloxycarbonyl)-amino]-$N^2$-(tert-butyloxy-carbonyl)-phenyl-alanine and (2S)-2-cyano-pyrrolidine.

EXAMPLE 29

N-{4-[(2S)-2-Amino-3-oxo-3-(1-pyrrolidinyl)-propyl]-phenyl}-N'-nitroguanidine hydrochloride Step A: 4-[(2S)-2-[(Tert-butyloxycarbonyl)-amino]-3-oxo-3-(1-pyrrolidinyl)-propyl]-aniline The expected product is obtained according to the process described in Step A of Example 1, starting from (2S)-2-[(tert-butyloxycarbonyl)-amino]-3-(4-aminophenyl)-propanoic acid and pyrrolidine.

Step B: N-{4-[(2S)-2-[(Tert-butyloxycarbonyl)-amino]-3-oxo-3-(1-pyrrolidinyl)-propyl]-phenyl}-N'-nitroguanidine The expected product is obtained by reacting the compound obtained in the preceding Step with N-methyl-N'-2-dioxohydrazinecarboximidohydrazide-2-oxide, according to the process described in J. Am. Chem. Soc. 1949, 71, 1968–1970.

Step C: N-{4-[(2S)-2-Amino-3-oxo-3-(1-pyrrolidinyl)-propyl]-phenyl}-N'-nitroguanidine hydrochloride The expected product is obtained according to the process described in Step B of Example 1, starting from the compound obtained in the preceding Step B.

Elemental microanalysis:

|  | C % | H % | N % | Cl % |
|---|---|---|---|---|
| calculated | 47.13 | 5.93 | 23.55 | 9.94 |
| found | 48.06 | 5.77 | 23.60 | 10.00 |

EXAMPLE 30

N-[(6S)-6-Amino-7-(1,3-thiazolidin-3-yl)-7-oxoheptyl]-N'-nitroguanidine dihydrochloride The expected product is obtained according to the process described in Example 29, starting from (2S)-2-[(tert-butyloxycarbonyl)-amino]-7-amino-heptanoic acid and 1,3-thiazolidine.

Elemental microanalysis:

|  | C % | H % | N % | S % | Cl % |
|---|---|---|---|---|---|
| calculated | 34.73 | 6.28 | 22.09 | 8.43 | 15.84 |
| found | 34.78 | 6.19 | 21.24 | 8.58 | 15.56 |

EXAMPLE 31

N-[(6S)-6-Amino-7-[(2S)-2-cyano-1-pyrrolidinyl]-7-oxoheptyl]-N'-nitroguanidine hydrochloride The expected product is obtained according to the process described in Example 29, starting from (2S)-2-[tert-butyloxycarbonyl)-amino]-7-amino-heptanoic acid and (2S)-2-cyano-pyrrolidine.

| Elemental microanalysis: | | | | |
|---|---|---|---|---|
| | C % | H % | N % | Cl % |
| calculated | 43.15 | 6.69 | 27.10 | 9.80 |
| found | 43.75 | 6.59 | 26.93 | 9.94 |

EXAMPLE 32

N-{4-[(2S)-2-Amino-3-oxo-3-[(2S)-2-cyano-1-pyrrolidinyl]-propyl]-phenyl}-N'-nitroguanidine hydrochloride The expected product is obtained according to the process described in Example 29, starting from (2S)-2-[(tert-butyloxycarbonyl)-amino]-3-(4-aminophenyl)-propanoic acid and (2S)-2-cyano-pyrrolidine.

PHARMACOLOGICAL STUDY OF THE COMPOUNDS OF THE INVENTION

EXAMPLE 33

In vitro Inhibition of Dipeptidyl Peptidase IV

The effect of the compounds on the in vitro enzymatic activity of DPPIV is evaluated as follows. The enzyme, from pig kidney, is assayed using a chromogenic substrate, glycyl-prolyl-p-nitroanilide 1.4 mM, which is hydrolysed to release p-nitroaniline, which absorbs at 405 nm. The activity of the enzyme is determined by absorbance, in the presence of variable concentrations of the compound being evaluated (mostly from $10^{-4}$ to $10^{-9}$M). The data obtained allow the effective dose for 50% inhibition of the control activity ($IC_{50}$) to be determined. The compounds of the invention have an $IC_{50}$ of from 1 nM to 10 $\mu$M.

EXAMPLE 34

Pharmaceutical Composition

| Formulation for the preparation of 1000 tablets each containing a dose of 10 mg | |
|---|---|
| Compound of Example 1 | 10 g |
| Hydroxypropylcellulose | 2 g |
| Wheat starch | 10 g |
| Lactose | 100 g |
| Magnesium stearate | 3 g |
| Talc | 3 g |

We claim:

1. A compound selected from those of formula (I):

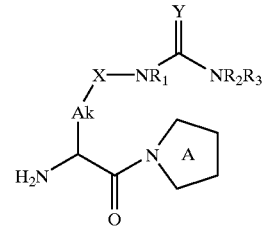

(I)

wherein:

represents a 5-membered nitrogen-containing heterocycle optionally substituted by cyano,
Ak represents a linear or branched ($C_1$–$C_6$)alkylene chain,
X represents a single bond or phenylene,
$R_1$ and $R_2$, which may be identical or different, each represent hydrogen or linear or branched ($C_1$–$C_6$)alkyl,
Y represents $NR_4$ or CH—$NO_2$,
$R_4$ represents hydrogen or linear or branched ($C_1$–$C_6$) alkyl,
$R_3$ represents:
  a group selected from linear or branched ($C_1$–$C_6$)alkyl, nitro and cyano, when Y represents CH—$NO_2$, or
  a group selected from nitro and cyano, when Y represents $NR_4$,
  its tautomers when they exist, its optical isomers, and addition salts thereof with a pharmaceutically acceptable acid,
with the exclusion of compounds wherein, simultaneously,

represents an unsubstituted 5-membered nitrogen-containing heterocycle, Ak represents —($CH_2$)$_3$—, X represents a single bond, Y represents NH and $R_3$ represents nitro,
it being understood that the term "5-membered nitrogen-containing heterocycle" is understood to mean a 5-membered saturated monocyclic group containing one, two or three hetero atoms, one of which hetero atoms is nitrogen, and any additional hetero atoms present are selected from oxygen, nitrogen and sulphur.

2. A compound of

claim 1 wherein represents 1-pyrrolidinyl optionally substituted by a group selected from cyano or 1,3-thiazolidin-3-yl optionally substituted by cyano.

3. A compound of claim 1 wherein the configuration α to the amide function is (S).

4. A compound of claim 1 wherein Ak represents $(CH_2)_4$.

5. A compound

of claim 1 wherein represents 1-pyrrolidinyl optionally substituted by a group selected from cyano or 1,3-thiazolidin-3-yl optionally substituted by cyano, and Ak represents $(CH_2)_3$.

6. A compound of claim 1 wherein X represents a single bond.

7. A compound of claim 1 wherein Y represents $NR_4$, wherein $R_4$ represents hydrogen or linear or branched $(C_1-C_6)$alkyl.

8. A compound of claim 1 wherein $R_3$ represents nitro.

9. A compound of claim 1 which is N-{(4S)-4-amino-5-[(2S)-2-cyano-1-pyrrolidinyl]-5-oxopentyl}-N'-nitroguanidine.

10. A compound of claim 1 which is N-{(5S)-5-amino-6-[(2S)-2-cyano-1-pyrrolidinyl]-6-oxohexyl}-N'-nitroguanidine.

11. A compound of claim 1 which is N-{(5S)-5-amino-6-(1,3-thiazolidin-3-yl)-6-oxohexyl-N'-nitroguanidine.

12. A pharmaceutical composition comprising a compound as claimed in claim 1, together with pharmaceutically acceptable excipients or vehicles.

13. A method of treating a living animal body afflicted with a condition selected from glucose intolerance or disorders associated with hyperglycemia selected from type II diabetes and obesity, comprising the step of administering to the living animal body an amount of a compound of claim 1 which is effective for alleviation of said condition.

* * * * *

UNITED STATES PATENT AND TRADEMARK OFFICE
CERTIFICATE OF CORRECTION

PATENT NO.    : 6,706,742 B2
DATED         : March 16, 2004
INVENTOR(S)   : Guillaume DeNanteuil et al.

It is certified that error appears in the above-identified patent and that said Letters Patent is hereby corrected as shown below:

<u>Title page,</u>
Item [73], Assignee, "Les Laboratories Servier" should be
-- Les Laboratoires Servier --.

<u>Column 16,</u>
Line 63, "A compound of  Claim 1 wherein represents" should be -- A compound of Claim 1 wherein  represents --.

<u>Column 17,</u>
Line 2, "A compound of  Claim 1 wherein represents" should be -- A compound of claim 1 wherein  represents --.

Signed and Sealed this

Twenty-second Day of February, 2005

JON W. DUDAS
*Director of the United States Patent and Trademark Office*